US008876885B2

(12) United States Patent
Lootz et al.

(10) Patent No.: US 8,876,885 B2
(45) Date of Patent: Nov. 4, 2014

(54) STENT

(75) Inventors: Daniel Lootz, Rostock (DE); Bettina Surber, Duebendorf (CH); Mathias Haussmann, Zurich (CH)

(73) Assignee: BIOTRONIK VI Patent AG, Baar (CH)

( * ) Notice: Subject to any disclaimer, the term of this patent is extended or adjusted under 35 U.S.C. 154(b) by 1755 days.

(21) Appl. No.: 12/108,571

(22) Filed: Apr. 24, 2008

(65) Prior Publication Data
US 2008/0269872 A1 Oct. 30, 2008

(30) Foreign Application Priority Data

Apr. 26, 2007 (DE) .......................... 10 2007 019 703

(51) Int. Cl.
*A61F 2/06* (2013.01)
*A61F 2/915* (2013.01)

(52) U.S. Cl.
CPC .......... *A61F 2/915* (2013.01); *A61F 2002/9155* (2013.01); *A61F 2002/91591* (2013.01); *A61F 2250/0071* (2013.01)
USPC ........................................ 623/1.15; 623/1.16

(58) Field of Classification Search
USPC ................ 623/1.11–1.15, 1.2, 1.16
See application file for complete search history.

(56) References Cited

U.S. PATENT DOCUMENTS

| | | | | |
|---|---|---|---|---|
| 6,197,047 B1 * | 3/2001 | Kranz | ........................... | 623/1.15 |
| 2002/0111671 A1 * | 8/2002 | Stenzel | ......................... | 623/1.16 |
| 2003/0199969 A1 * | 10/2003 | Steinke et al. | ............... | 623/1.16 |
| 2004/0149294 A1 * | 8/2004 | Gianchandani et al. | ...... | 128/879 |
| 2006/0111772 A1 * | 5/2006 | White et al. | ................. | 623/1.15 |
| 2006/0122694 A1 | 6/2006 | Stinson et al. | | |
| 2006/0195175 A1 * | 8/2006 | Bregulla | ....................... | 623/1.15 |
| 2007/0005127 A1 * | 1/2007 | Boekstegers et al. | ........ | 623/1.16 |
| 2007/0073383 A1 | 3/2007 | Yip et al. | | |
| 2008/0195190 A1 * | 8/2008 | Bland et al. | ................. | 623/1.11 |
| 2008/0215135 A1 * | 9/2008 | Seguin et al. | ................ | 623/1.35 |

FOREIGN PATENT DOCUMENTS

| | | |
|---|---|---|
| DE | 10325128 A1 | 1/2005 |
| EP | 1034751 A2 | 9/2000 |
| EP | 1430854 A1 | 6/2004 |
| WO | 0015151 A1 | 3/2000 |
| WO | 02065949 A2 | 8/2002 |

(Continued)

OTHER PUBLICATIONS

Search Report for German Patent Application No. 10 2007 019 703.0; Apr. 26, 2007.

(Continued)

*Primary Examiner* — Dianne Dornbusch
*Assistant Examiner* — Alexander Orkin
(74) *Attorney, Agent, or Firm* — Greer, Burns & Crain, Ltd.

(57) ABSTRACT

A stent comprising an essentially tubular open supporting structure (4) of interconnected trusses (9), whereby the supporting structure (4) can be widened radially with deformation of the trusses (9) for application of the stent, and predetermined breaking points (14) in the supporting structure (4) for fragmentation of the stent after application, and the ends (10, 11) of the trusses (9) that are adjacent to the respective predetermined breaking point (14) having a joint design and which are provided in the area of the predetermined breaking point (14), such that the ends (10, 11) of the trusses (9) are held together with articulation under an applied pressure with the predetermined breaking point (14) broken.

12 Claims, 3 Drawing Sheets

(56) References Cited

FOREIGN PATENT DOCUMENTS

| WO | 2006020649 | A1 | 2/2006 |
|---|---|---|---|
| WO | 2006089739 | A1 | 8/2006 |
| WO | 2006116383 | A2 | 11/2006 |
| WO | 2006138010 | A2 | 12/2006 |

OTHER PUBLICATIONS

Search Report for European Patent Application No. 08006201.1; Aug. 27, 2009.

* cited by examiner

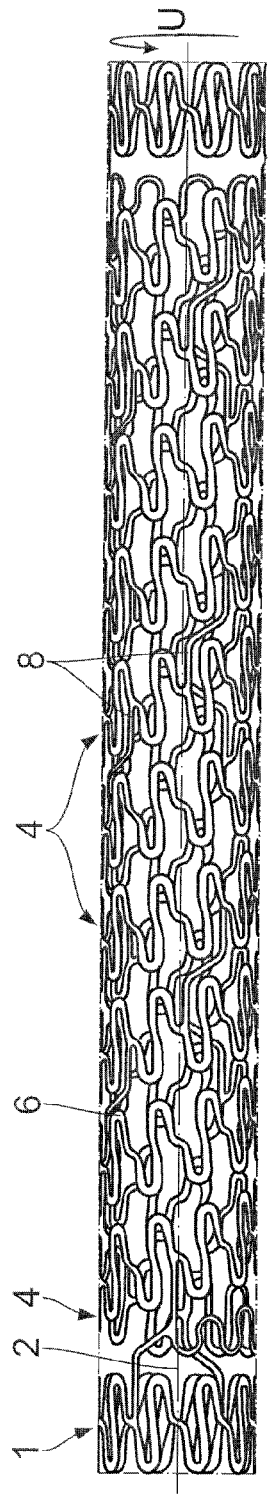
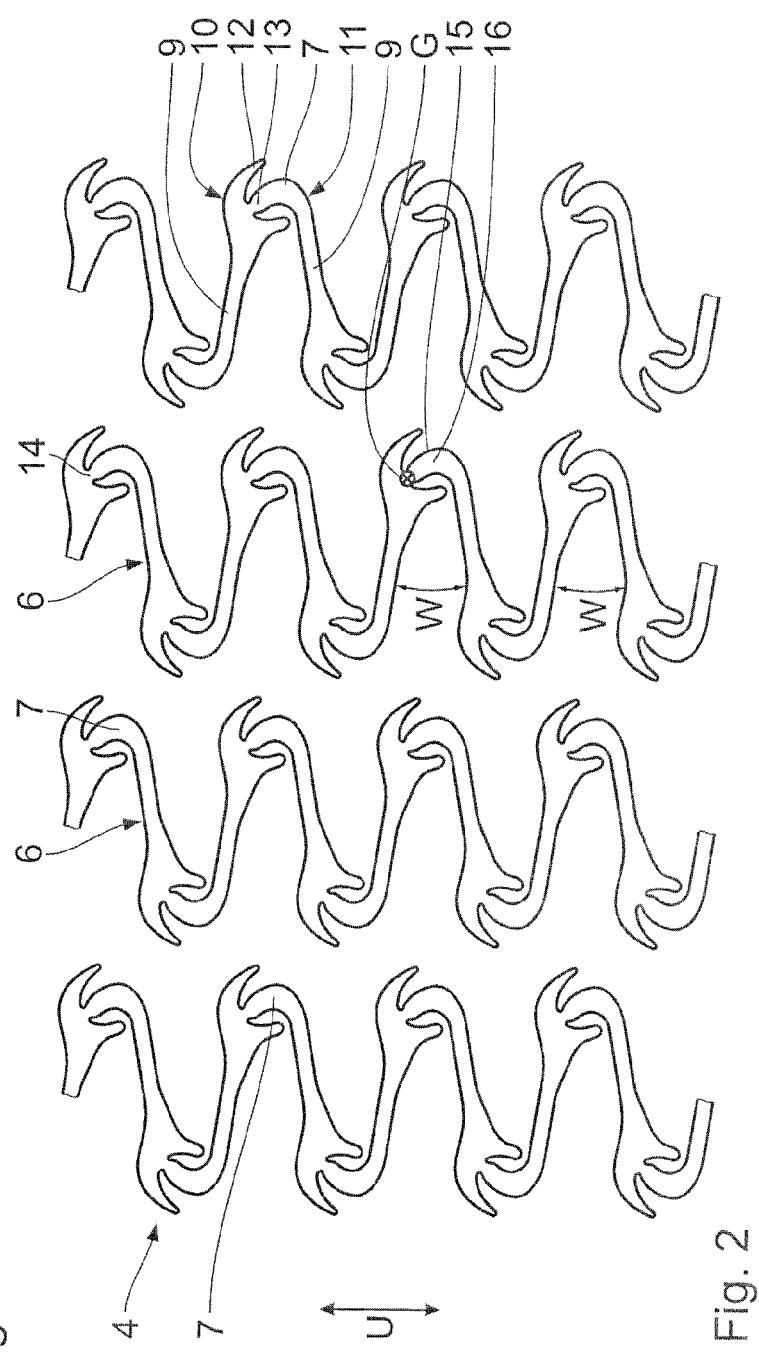
Fig. 1
Fig. 2

STENT

PRIORITY CLAIM

This patent application claims priority to German Patent Application No. 10 2007 019 703.0, filed Apr. 26, 2007, the disclosure of which is incorporated herein by reference in its entirety.

FIELD

The present disclosure relates to stents.

BACKGROUND

Stents are well known in the art. U.S. Patent Publication No. 2006/0122694 A1, for example, discloses a stent which comprises an essentially tubular open supporting structure of interconnected webs. This supporting structure is radially distensible with deformation of the webs formed by interconnected trusses in sections for application of the stent in a blood vessel in a patient.

With the previously known stent, predetermined breaking points are also integrated into the supporting structure, serving to fragment the stent after application. As mentioned in the U.S. patent publication cited above, this fragmentation serves to break apart the electrically conductive conductor loop formed by the peripheral trusses to thereby increase the visibility of the body material in the lumen surrounded by the stent in a magnetic resonance examination. Since the integrity of the webs is still guaranteed during application of the stent, this stent has enough stability to ensure the desired vasodilation through its application.

With the known stent, the predetermined breaking points are formed by bridges of material within the stent webs made of a material having a greater corrodability. As an alternative to this, the predetermined breaking points may be formed by a cross-sectional constriction which leads to a defined dissolution of the structural stability of the stent in the area of the predetermined breaking point due to the corrosion of the stent that occurs there.

The more recent development in the field of stents provides for the use of magnesium and its alloys as the materials. These materials are biodegradable and thus lead to the desired dissolution of the stent after widening the blood vessel and its inherent stabilization. This prevents the problem whereby the stent, acting as a foreign body, tends to an accumulation of cells over a period of time, and therefore the treated blood vessel becomes occluded by a restenosis.

Magnesium and its alloys are, however, at risk of breakage under corrosive stress and/or vibrating stress at the same time, such as that to which a stent administered in a pulsating bloodstream is exposed. In addition, local spots of corrosion may occur, e.g., due to irregularities in the material or the surface. Stents such as those known from European Patent Application No. 1 430 854 A1, for example, may thus be subject to the risk of uncontrolled fragmentation after initial deformation for radial widening of the stent so that the supportive function of such a stent is at risk, in particular, in the arterial blood vessels. The reason for this is that individual web elements in the area of uncontrolled fragmentation no longer have a structural mechanical cohesion and the supportive function of the stents is lost with an increasing number of fragments formed.

SUMMARY

The present disclosure describes several exemplary embodiments of the present invention.

One aspect of the present disclosure provides a stent comprising a) an essentially tubular open supporting structure of interconnected trusses, each truss having a first end and a second end, whereby the supporting structure can be widened radially with deformation of the trusses for application of the stent; b) predetermined breaking points in the supporting structure for fragmentation of the stent after application; and, c) the ends of the trusses that are adjacent to the respective predetermined breaking point which is provided in the area of the predetermined breaking point, having a joint design such that the ends of the trusses are held together with an articulation under an applied pressure with the predetermined breaking point broken.

Based on the disadvantages associated with the state of the art as described here, the present disclosure provides a stent which prevents or reduces uncontrolled fragmentation, in particular, when using a material for a stent that is at risk of breakage.

This is achieved by the features of the present disclosure whereby an articular embodiment of the ends adjacent to the respective predetermined breaking point of the trusses forming the webs is provided such that the ends of the trusses are held together in an articulated manner when the predetermined breaking point is broken under a pressure acting on the stent.

The present disclosure is thus based on a diametrically opposite concept in comparison with the state of the art, namely, controlled fragmentation in the area of the predetermined breaking points of the supporting structure takes place in such a way that the point in time of the local breaking of the stent areas takes place in a defined manner and is controllable through the shape of the stent. Through the design of the joint in the area of the predetermined breaking points, in this context a weakening of the structure is avoided to the extent that the stent can still maintain its supporting effect for a sufficiently long period of time despite the fragmentation. The reason for this is the controlled joining of the adjacent ends of the truss at the predetermined breaking point due to the radial load originating from the blood vessel. The trusses thus act with a supporting effect under pressure radially despite the loss of integration.

Another advantage of this controlled fragmentation is that the stent is better adaptable in its structure to materials having a reduced elongation at break and/or tensile strength or bending strength. The controlled fragmentation leads to a reduction in stress in the areas that are under load radially, so that uncontrolled stress corrosion can no longer occur.

BRIEF DESCRIPTION OF THE DRAWINGS

Various aspects of the present disclosure are described hereinbelow with reference to the accompanying figures in which like reference characters represent the same or similar parts throughout the several views, of which:

FIG. 1 is a longitudinal side view of a stent according to one exemplary embodiment;

FIG. 2 is a schematic view of a detail in a developed representation of four rows of webs of the stent of FIG. 1 in a contracted state;

DETAILED DESCRIPTION

Figure 3:
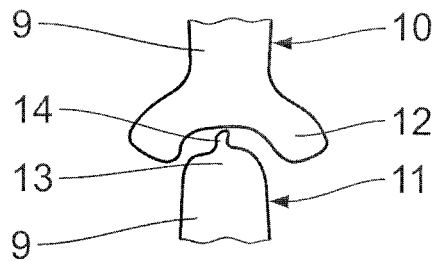
FIG. 3 is a schematic view of a neighboring truss end in the area of a predetermined breaking point during and after fragmentation.
Figure 4:
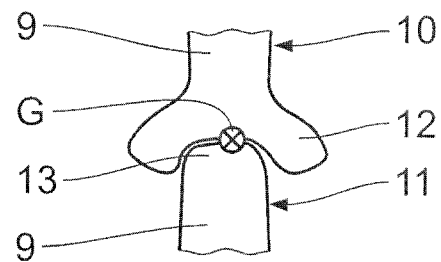
FIG. 4 is a schematic view of a second neighboring truss end in the area of a predetermined breaking point during and after fragmentation.

FIG. 1 shows a stent 1 having a basic cylindrical shape with a longitudinal axis 2. The circumferential wall of the stent is formed by an open tubular supporting structure 4 consisting of interconnected webs 6. These webs 6 have a helical primary shape in the circumferential direction U. As this superimposed secondary shape, the webs 6 are designed to be meandering in the circumferential direction, whereby the meandering curves have zeniths 7 pointing toward the stent ends. In isolated positions, the webs 6 running side by side are interconnected by axial connectors 8. The entire latticework of the supporting structure 4 is shaped out of a cylindrical blank, e.g., made of a magnesium alloy, by laser cutting.

FIG. 2 shows the fine structure of the webs 6 that were omitted from FIG. 1 in greater detail for the sake of simplicity. The meandering shape of the webs 6 is composed of zigzag-shaped trusses 9 going back and forth between the zeniths 7 in sections. The ends 10, 11 of the trusses 9 have different structures. The one truss end 10 is designed with a shape 12 like a joint socket while the opposite end 11 is designed as a joint ball 13. The joint ball 13 is situated at the end of a bend 16 provided with an external rounded surface 15. The diameter of the joint ball 13 is definitely smaller than the inside diameter of the joint socket 12. The joint socket 12 and joint ball 13 are referred to as two-dimensional with respect to the actual joint site because the entire structure of the stent is cut out of the lateral surface of the aforementioned blank so that joint axis G is directed radially.

As FIG. 3 shows clearly, a one-piece breaking web 14, which functions as the predetermined breaking point for the supporting structure 4 within the joint design comprising the joint socket 12 and the joint ball 13, is provided between the joint socket 12 and the joint ball 13. Due to their small width, the narrow breaking webs 14 have a cross-sectional area that is many times smaller than that of the actual web.

As shown clearly in FIGS. 2-5, the angles W between the trusses 9 are greatly increased by bending in the expansion of the stent 1 during application of the stent in a blood vessel. The bending moment exerted on the trusses ensures breaking of the breaking webs 14 so the predetermined breaking points within the webs 6 are released. Under the radial pressure exerted by the blood vessel on the stent 1, the joint balls 13 come to lie cleanly in the corresponding joint sockets 12 and are thus held together like a joint. This means that the widening of the stent can be accomplished without having problematical stress peaks act on the stent structure. The forces holding the joint socket 12 and the joint ball 13 together are created by the radial force acting on the stent due to the blood vessel are indicated by arrow 19 in FIG. 5.

Figure 6:
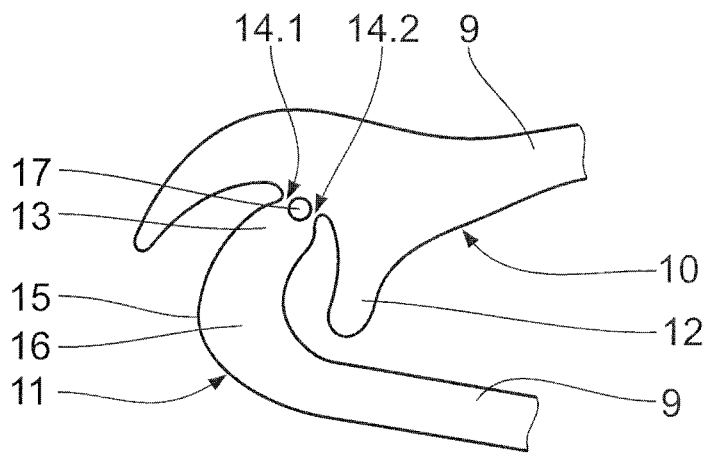
FIG. 6 is a schematic enlarged view of the ends of two neighboring trusses with a predetermined breaking point in a first alternative embodiment.
Figure 7:
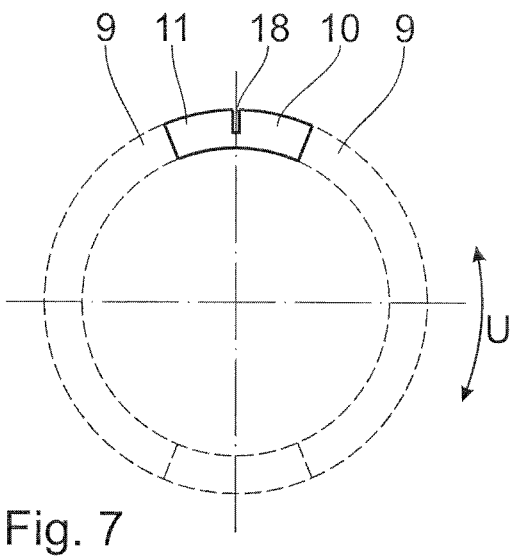
FIG. 7 is a schematic radial section through a stent with a predetermined breaking point in a second alternative embodiment.
Figure 5:
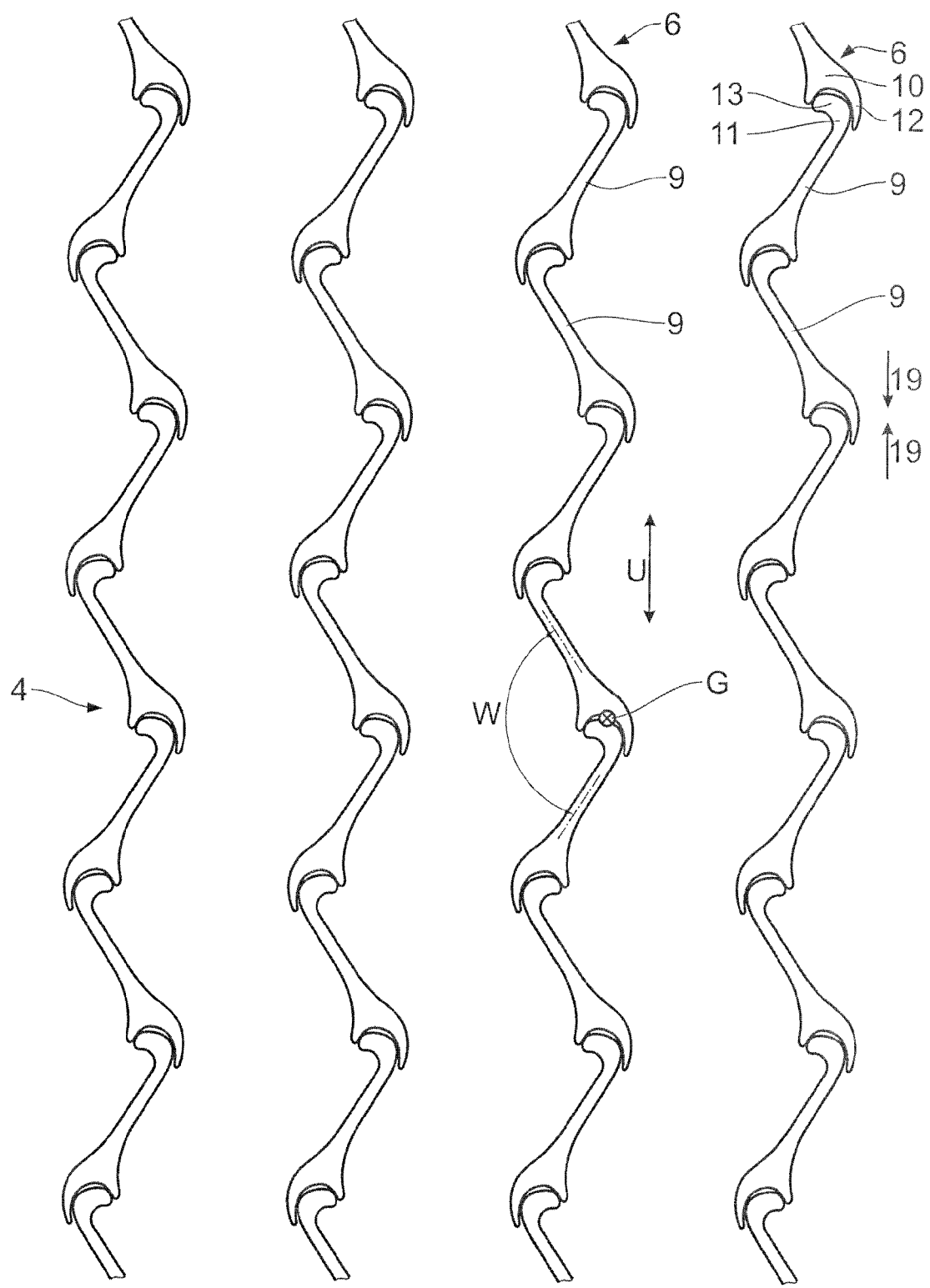
FIG. 5 is a view of the four rows of stents as shown in FIG. 2 in an expanded state of the stent.

In the exemplary embodiment shown in FIG. 6, the predetermined breaking point is formed between the two ends 10, 11 of two neighboring trusses 9 through a through-hole 17 created radially in the supporting structure so that two breaking webs 14.1, 14.2 running side by side are provided. As an exemplary alternative, a predetermined breaking point may be provided between two neighboring ends 10, 11 of the trusses 9 through a blind hole or a blind slot 18, as shown in FIG. 7.

In general, a reduction in cross section to 10% of the cross-sectional area of the trusses 9 can be implemented. This depends on the particular material used and can be determined by simple experiments.

All patents, patent applications and publications referred to herein are incorporated by reference in their entirety.

What is claimed is:

1. A stent, comprising:
   a) an essentially tubular open supporting structure of interconnected zigzag-shaped trusses which form meandering curved webs in the circumferential direction, each truss having a first end and a second end, whereby the supporting structure can be widened radially with deformation of the trusses for application of the stent;
   b) an angularly articulatable joint connecting adjacent trusses and defined by a first end of a first truss and a second end of a second truss, the first end having a wall portion defining generally U-shaped opening, the second end having a generally rounded shape, the second end positioned within and maintained in a pre-expansion first angle with the first end U-shaped opening by a breaking point connector connecting the second end and the wall portion proximate to the middle of the U-shaped opening, wherein the breaking point connector can release from either the first or second end in response to deformation of the stent during expansion, whereupon the second end can angularly pivot within the U-shaped opening of the first end to create a second angle greater than the first angle, while the first end and second end are maintained in substantially the same proximity to each other as before expansion by radial force.

2. The stent of claim 1, wherein the ends of the trusses adjacent to a respective predetermined breaking point connector are designed as a joint socket with a joint socket shape on one truss end and a shape like a joint ball on the second truss end.

3. The stent of claim 2, wherein the joint socket has a joint axis running radially with respect to the stent.

4. The stent of claim 2, wherein the joint ball shape is formed by an externally rounded bend of the truss end.

5. The stent of claim 1, wherein the breaking point connector has a smaller width in comparison to the trusses.

6. The stent of claim 1, wherein the breaking point connector has a smaller thickness in comparison to the trusses.

7. The stent of claim 1, wherein the breaking point connector comprises at least two breaking point connector portions.

8. The stent of claim 1, further comprising a plurality of webs running in a meandering pattern in the peripheral direction and having zeniths, wherein each predetermined breaking point connector is arranged with the joint design in the area of the zeniths of the webs.

9. The stent of claim 1, wherein the webs having a smaller cross-sectional area in comparison to the trusses.

10. The stent of claim 1, wherein the webs have a helical primary shape in a circumferential direction.

11. The stent of claim 1, wherein the webs are interconnected by axial connectors.

12. A stent, comprising:
   a) an essentially tubular open supporting structure of interconnected zigzag-shaped trusses which form meandering curved webs in the circumferential direction, each truss having a first end and a second end, whereby the supporting structure can be widened radially with deformation of the trusses for application of the stent, the webs being interconnected by axial connectors;
   b) an angularly articulatable joint connecting adjacent trusses and defined by a first end of a first truss and a second end of a second truss, the first end having a wall portion defining generally U-shaped opening, the second end having a generally ball shape, the second end positioned within and maintained in a pre-expansion first angle with the first end U-shaped opening by at least one breaking point connector connecting the second end and the wall portion proximate to the middle of the U-shaped opening, the at least one breaking point connector having a width and thickness smaller than that of a truss, wherein the at least one breaking point connector can release from either the first or second end in response to deformation of the stent during expansion, whereupon the second end can angularly pivot within the U-shaped opening of the first end to create a second angle greater than the first angle, while the first end and second end are maintained in substantially the same proximity to each other as before expansion by radial force.

* * * * *